United States Patent [19]

Atad

[11] Patent Number: 5,762,202
[45] Date of Patent: Jun. 9, 1998

[54] TRAY FOR HOLDING MEDICAL AND DENTAL INSTRUMENTS

[76] Inventor: Jack Atad, 34 Lascov Street, Haifa 34950,, Israel

[21] Appl. No.: 854,333

[22] Filed: May 12, 1997

[51] Int. Cl.⁶ .................. A61L 2/20; B65D 81/18
[52] U.S. Cl. .............. 206/756; 206/369; 206/370; 422/300
[58] Field of Search .................. 206/363, 368, 206/369, 370, 438, 570, 756, 762; 422/297, 300

[56] References Cited

U.S. PATENT DOCUMENTS

| | | | |
|---|---|---|---|
| 2,472,028 | 5/1949 | Son | 422/300 |
| 4,229,420 | 10/1980 | Smith | 206/370 |
| 4,342,391 | 8/1982 | Schainholz | 206/370 |
| 4,577,755 | 3/1986 | Ramsay | 206/370 |
| 4,959,199 | 9/1990 | Brewer | 206/1.5 |
| 5,084,251 | 1/1992 | Thomas | 206/557 |
| 5,433,929 | 7/1995 | Riihimaki et al. | 206/369 |
| 5,449,069 | 9/1995 | Pijanowski et al. | 206/370 |
| 5,451,380 | 9/1995 | Zinnanti | 206/370 |

*Primary Examiner*—Jimmy G. Foster
*Attorney, Agent, or Firm*—Frishauf, Holtz, Goodman, Langer & Chick

[57] ABSTRACT

The tray is designed to hold medical and dental instruments in firm and parallel alignment during transport and sterilization and to be opened for ready withdrawal or placing of such instruments. It includes a main part in the form of a rectangular bottom surrounded by upstanding rims along both side edges and along its rear edge of which the rear rim is higher than the side rims and forms a channel-shaped pocket configured to cover the heads of the instruments. Two serrated strips are firmly attached to the bottom in parallel spaced-apart alignment with the serrations serving to support and hold the instruments in position. A trough-shaped front cover is pivotally attached to the side rims and can be swung from a top position covering the front ends of the instruments into a position underneath the bottom serving to raise the front of the tray into rearwardly inclined position.

10 Claims, 4 Drawing Sheets

TRAY FOR HOLDING MEDICAL AND DENTAL INSTRUMENTS

The invention relates to a tray for holding various medical and dental instruments permitting ready access to each instrument in its normally open state, while being provided with locking means securing these instruments in position during transport and/or sterilization.

BACKGROUND OF THE INVENTION

A doctor who requires a specific instrument during examination or operation of a patient, either asks the nurse to hand it to him, or in case he works alone he has to look for it and to select one from the tray on which the instruments are spread out in more or less random order. In all cases where the doctor or dentist requires instruments to be handled in a certain order, it becomes quite difficult and time-absorbing to find the correct item. For this purpose certain types of instruments are wrapped in holders made of cloth, plastics or paper permitting the doctor to select the proper tool with less effort. On the other hand, since all medical and dental instruments have to be sterilized before every use, they are usually laid out on a flat tray and inserted into the sterilizer, from where they are taken out later on and selected for their specific task. Now, there exist certain instruments which are being used consecutively in a given order, and this requires an effort to re-arrange them after each sterilization.

For the above reasons it is the main object of the present invention to provide a tray on which specific instruments are positioned in the order required and handled by the doctor, be he a surgeon, an obstetrician or a dentist, and wherein these instruments are held in firm position during transport between operating rooms, sterilization and storage.

It is a further object to provide a tray permitting ready placing of each instrument according to size and/or timely use and easy withdrawal of each instrument at the desired moment.

Still another object is to provide a tray so designed that contact with each instrument is in two points only.

And it is a final object to provide a tray permitting transport and sterilization of the enclosed instruments in their placed order without the possibility of any instrument slipping from its place or falling out of the tray.

On the other hand the tray should be of simple design, easy to clean and suitable for use in every clinic, laboratory or hospital.

SUMMARY OF THE DISCLOSURE

The tray is designed to hold a plurality of medical and dental instruments in spaced-apart parallel alignment. It has a front facing the doctor and a rear with the instruments placed with their grips lying in front and their heads close to the rear of the tray. The tray comprises a main body end a pivotally attached portion closing the front which is openable to allow use of the instruments. The main body consists of a rectangular bottom including a raised rim along its rear edge and along its two lateral edges. Two rows of instrument-receiving means are attached to the bottom in spaced-apart alignment substantially parallel to the rear edge of the tray. The rear of the tray forms a channel-shaped pocket for the heads of the instruments in the form of a strip of material of a length co-extensive with the rear edge and of a width adapted to cover the heads of the instruments; it is preferably integral with the rear rim and connected to the rear portions of the side rims. It is provided with means allowing viewing of the instrument heads, such as a row of perforations in the top portion.

The movable portion is in the shape of a trough which is pivotally attached to the frontal portions of the side rims; during use of the instruments it is positioned underneath the front of the bottom and causes the tray to slightly slope in rearward direction. From this position it can be tilted in upward direction so as to cover a portion of the instrument grips and close the normally open front end of the tray.

The means for holding the instruments in parallel position preferably are in the form of two parallel serrated strips perpendicular to the bottom, wherein the serrations may be of different depth and width to accommodate different sizes of instruments. A typical example is a tray for Heger dilators which requires serrations of gradually increasing size from left to right of the tray.

The tray is made of a non-corrosive metal sheeting such as stainless steel, or of a plastics material which should preferably be transparent to enable viewing the instruments from all directions.

In the case of the tray being manufactured of metal the strip covering the rear end is perforated by a number of holes to permit viewing of the instruments, while with a transparent plastic this would not be necessary.

In a preferred embodiment the main body of the tray is stamped and bent from a single sheet of stainless steel, with the trough-shaped portion likewise stamped and bent from second steel sheet.

DETAILED DESCRIPTION OF THE DRAWINGS

Figure 1:
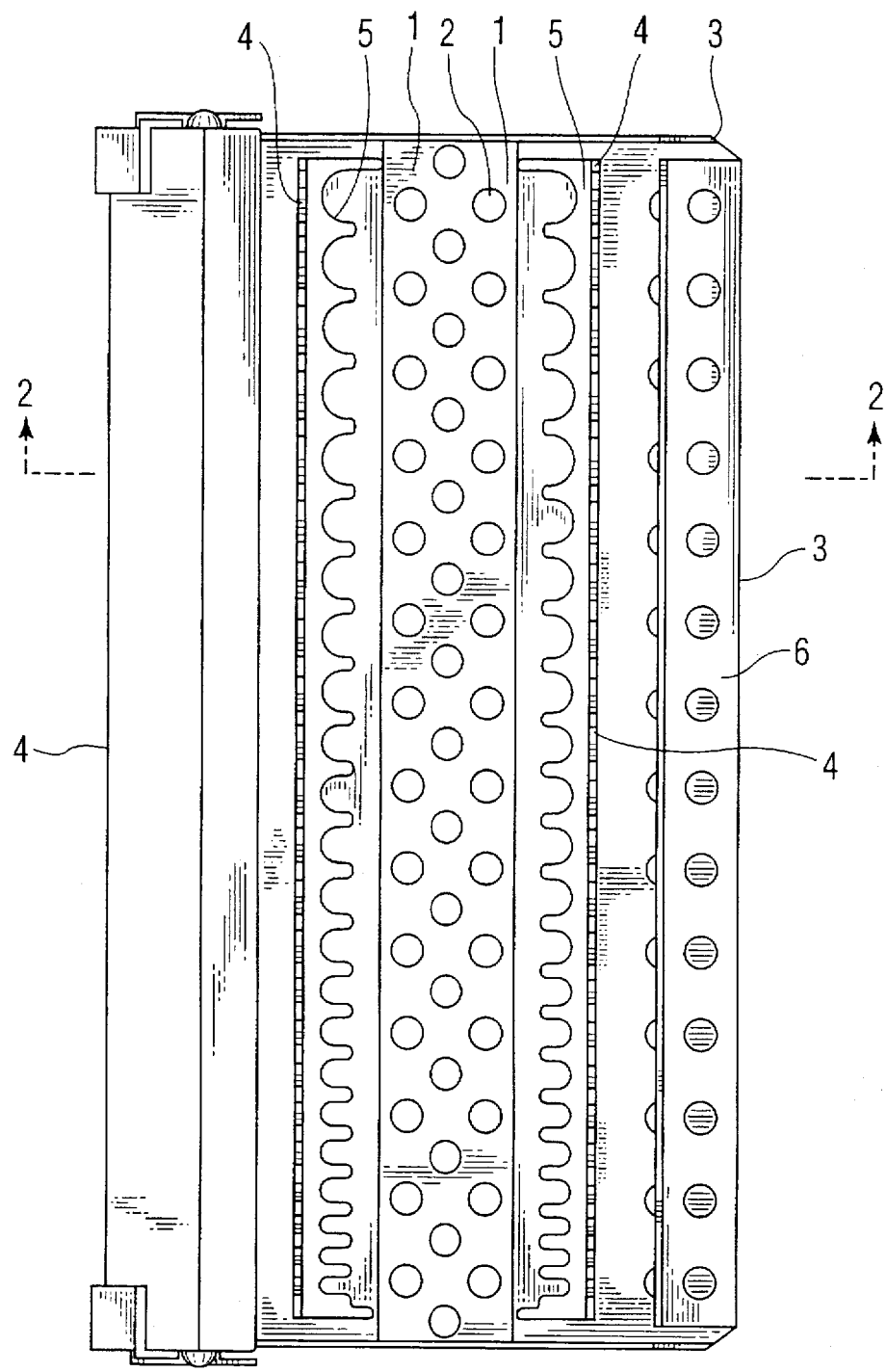
FIG. 1 is a plan via of the tray in closed position.

FIGS. 1 through 6 of the drawings illustrate a tray manufactured of metal sheeting by stamping and bending, but it will be understood that a tray of the same—or similar-shape and size may be manufactured by assembling several components. On the other hand the two parts of the tray can be manufactured by injection molding using a heat-resistant plastic material, which may be entirely, or partly, transparent.

The tray shown in FIGS. 1 through 5 comprises a main part I and a pivoted front cover II. Part I includes a rectangular bottom 1 which is perforated by a plurality of holes 2 and is surrounded along its rear edge and its two side edges by raised rims 3 and 3' respectively. Two rows of serrated strips 4 and 4' extend along the entire width of the tray in spaced apart alignment. In the present embodiment these strips are made by cutting and stamping them out of the bottom material and bending about a right angle into perpendicular position relative to the bottom surface. This can be clearly seen in FIGS. 4 and 5 which show the cut-out portions 5 and 5' in both projections. The rear of the tray forms a channel-shaped pocket for insertion of the head portions of the instruments. The pocket is formed by bending the sheet in continuation of the bottom portion into the rear rim 3, a cover strip 6 and a closure strip 7. The cover strip is perforated by a plurality of holes 8 which permit the user to view and to select the required instrument.

Figure 2:
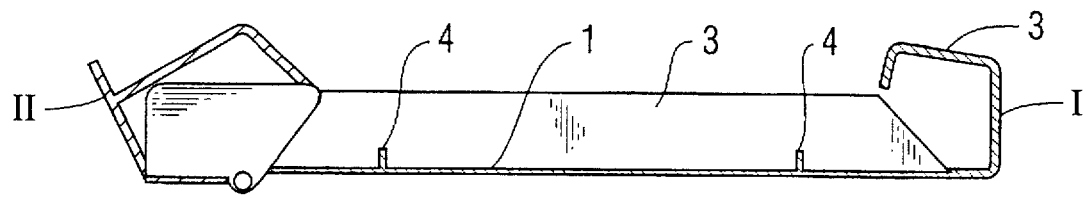
FIG. 2 is a section of the tray along line 2—2 of FIG. 1.
Figure 3:
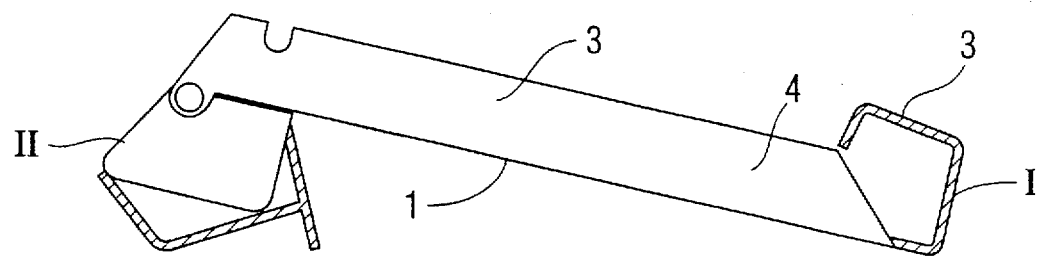
FIG. 3 is a side view of the tray of FIG. 1, in opened position.
Figure 4:
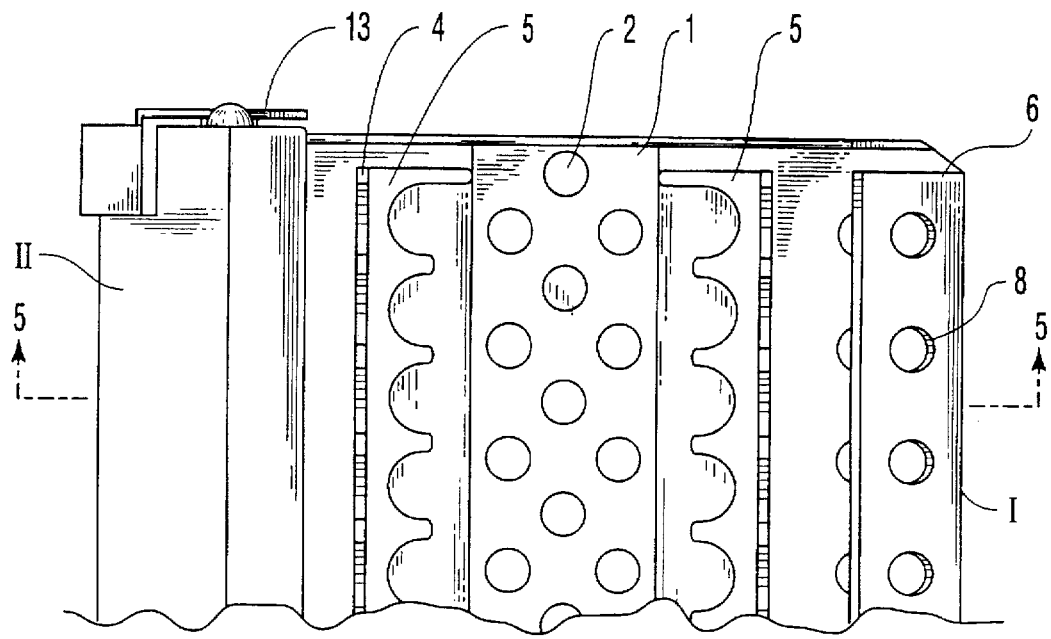
FIG. 4 is an enlarged plan view of one end of the tray shown in FIG. 1.
Figure 5:
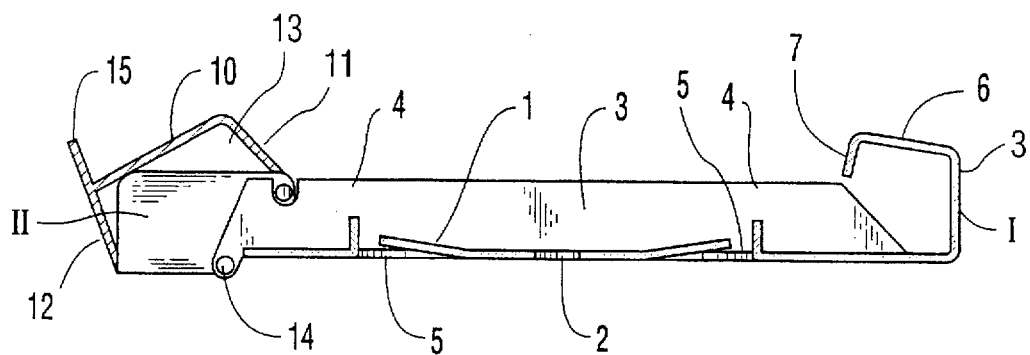
FIG. 5 is a section along line 5—5 of FIG. 4.
Figure 6:
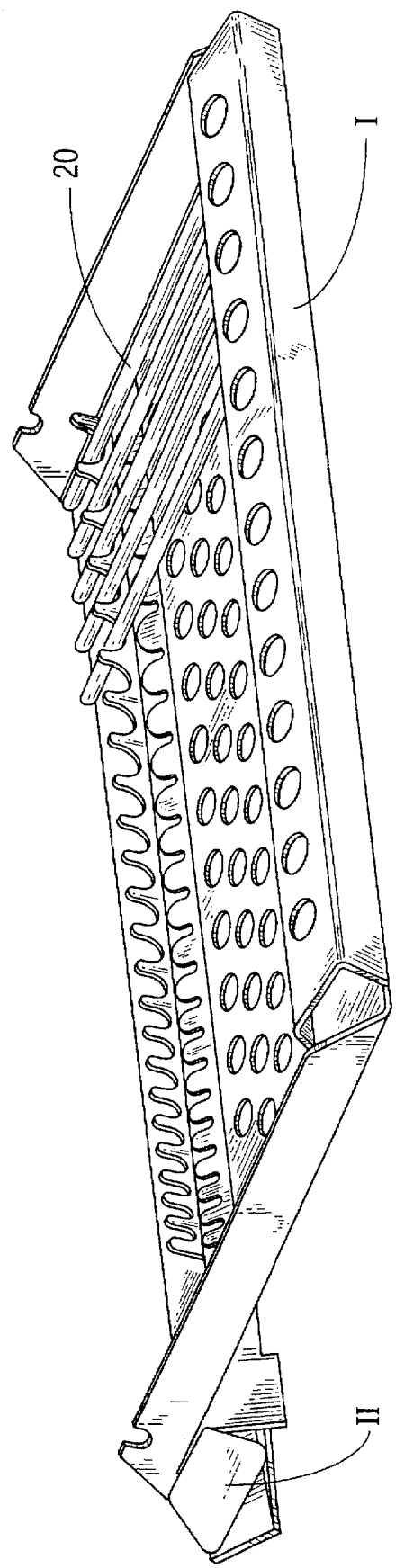
FIG. 6 is an isometric view of the tray of FIG. 1 in open position, showing a few instruments positioned at the far end of the tray.

Part II, the front cover, is in the shape of a trough formed of a bottom 10, a first side wall 11 and a second side wall 12. Two end walls 13 close the trough at both ends and are provided with pivots 14 permitting the cover to be tilted from a closing position as shown in FIGS. 2 and 5 into an open, support position as shown in FIGS. 3 and 6. In the closed position the cover forms a pocket in the front of the tray which covers the grip ends of the instruments and prevents them from slipping out during transport or sterilization. Side wall 12 extends beyond the bottom 10 to form a support in open state of the tray (v. FIGS. 3 and 6). In this open position, the tray is inclined this assists the user in selecting and taking the required instrument.

The isometric view of the open tray illustrated in FIG. 6 shows a few instruments 20 positioned in the serrations of strips 4 and 4'. The Figure also shows that the serrations in strings 4, 4' increase in width and depth from one side to the other which makes the tray especially suitable for use with cervix delators used one after the other during examination or operation by an obstetrician. It will be understood that the shape of the tray as illustrated and described in the foregoing may be modified in many respects, by maintaining the principle of the front cover serving alternately as front pocket and tray support. The present embodiment is unique since the two components are stamped and bent each from a single sheet of stainless steel. It is likewise feasable to assemble the tray from several parts. This applies more especially to the serrated strips which may be made separately and then attached to the bottom by rivetting or spot-welding.

I claim:

1. A tray designed for holding a plurality of medical or dental instruments in substantially parallel alignment, said tray being made of an inert heat-resistant material and having a rear end, a front end and two side edges, said tray having a normally open front end permitting placing or removing one or more of said instruments and having closing means holding said instruments in position for transporting or sterilizing said tray together with said instruments, said tray including, a rectangular bottom bordered by two raised rims along its side edges and a raised rim along its rear end, a channel-shaped pocket along its rear end covering a portion of the heads of said instruments and being provided with transparent portions permitting viewing of said heads means for holding said instruments in position, said means being firmly attached to said bottom, and a trough-shaped front cover of a length co-extensive with the front end of said tray, pivotally connected to the front of said side edges and adapted to be swung from a closing position covering the ends and parts of the grips of said instruments of said tray into an open position underneath said bottom permitting placing and removing one or more of said instruments.

2. The tray of claim 1, wherein placing of said front cover underneath said bottom causes inclination of said tray from a higher front to a lower rear end.

3. The tray of claim 1, wherein said means for holding said instruments in position are serrated strips of material firmly attached to said bottom, substantially perpendicular to the bottom surface.

4. The tray of claim 1, wherein said inert material is a non-corrosive metal in sheet form.

5. The tray of claim 4, wherein said metal is stainless steel sheeting.

6. The tray of claim 3, wherein said means for holding said instruments comprises stainless steel strips.

7. The tray of claim 6, wherein said steel strips are stamped and punched out of said bottom and bent into perpendicular position on said bottom.

8. The tray of claim 4, wherein said channel-shaped pocket along the rear is in the shape of a rear rim somewhat higher than the rims along the side edges, said rear rim being continued by a horizontal strip perforated by a plurality of holes and by a downwardly extending strip connected to a front edge of said perforated strip.

9. The tray of claim 1, wherein said material is a plastic material.

10. The tray of claim 9, wherein said plastic material is at least partly transparent.

* * * * *